(12) United States Patent
Suh et al.

(10) Patent No.: US 11,485,984 B2
(45) Date of Patent: Nov. 1, 2022

(54) METHOD FOR INTRODUCING HEPATOCYTE GROWTH FACTOR AND NEUROGENIN 1 INTO MESENCHYMAL STEM CELLS

(75) Inventors: Hae Young Suh, Gyeonggi-do (KR); Sung Soo Kim, Seoul (KR); Seung Wan Yoo, Seoul (KR); Young Don Lee, Gyeonggi-do (KR)

(73) Assignee: CELL & BRAIN CO., LTD, Jeollabuk-do (KR)

( * ) Notice: Subject to any disclaimer, the term of this patent is extended or adjusted under 35 U.S.C. 154(b) by 0 days.

(21) Appl. No.: 14/119,788

(22) PCT Filed: May 23, 2012

(86) PCT No.: PCT/KR2012/004082
§ 371 (c)(1),
(2), (4) Date: Nov. 22, 2013

(87) PCT Pub. No.: WO2012/161519
PCT Pub. Date: Nov. 29, 2012

(65) Prior Publication Data
US 2014/0086887 A1 Mar. 27, 2014

(30) Foreign Application Priority Data
May 23, 2011 (KR) .................. 10-2011-0048628

(51) Int. Cl.
| C12N 15/85 | (2006.01) |
| A61K 35/28 | (2015.01) |
| A61K 35/30 | (2015.01) |
| C12N 5/0775 | (2010.01) |
| C12N 15/86 | (2006.01) |

(52) U.S. Cl.
CPC .............. *C12N 15/85* (2013.01); *A61K 35/28* (2013.01); *A61K 35/30* (2013.01); *C12N 5/0663* (2013.01); *C12N 15/86* (2013.01); *C12N 2501/12* (2013.01); *C12N 2501/60* (2013.01); *C12N 2510/00* (2013.01)

(58) Field of Classification Search
CPC ...... C12N 5/0663; C12N 15/85; C12N 15/86; A61K 35/28
See application file for complete search history.

(56) References Cited

U.S. PATENT DOCUMENTS

| 2020/0190535 A1 | 6/2020 | Suh et al. |
| 2021/0310020 A1 | 10/2021 | Kim et al. |

FOREIGN PATENT DOCUMENTS

| EP | 2714896 A1 | 4/2014 |
| JP | 2007-284410 A | 11/2007 |
| WO | 02/074045 A2 | 9/2002 |
| WO | 2004016779 A1 | 2/2004 |
| WO | 2004050865 A1 | 6/2004 |
| WO | 2005040362 A1 | 5/2005 |
| WO | 2006011600 A1 | 2/2006 |
| WO | 2007122976 A1 | 11/2007 |
| WO | 2012/161519 A1 | 11/2012 |

OTHER PUBLICATIONS

Suh et al. ((kr1020040016785, abstract).*
Liu et al (J of Pediatric Surgery, 46: 537-545, 2011).*
Kim et al (Stem Cells, 26: 2217-2228, 2008.*
Zhao et al (Journal of Cerebral Blood Flow & Metabolism, 26: 1176-1188, 2006).*
http://en.wikipedia.org/wiki/Correlation_does_not_imply_causation. pp.1-8, printed Oct. 30, 2015).*
Thesaurus.com; printed Oct. 30, 2015, p. 1-3) Suspected Synonyms, Susp . . . ntonyms_ Thesaurus.*
Hiroshi et al (Current Signal Transduction Therapy, vol. 6, No. 2, 2011, Abstract).*
Ciervo et al, (Molecular Neurodegeneration, 12(85): 1-22, 2017) (Year: 2017).*
Kosztowski et al, (Expert Rev Anticancer Ther, 9(5): 597-612, 2009) (Year: 2009).*
Nguyen et al (Advanced Drug Delivery Reviews, p. 1-12, 2010) (Year: 2010).*
Piney et al, (Stem Cells, 25: 2896-2902, 2007) (Year: 2007).*
Jackson (J Postgrad Med, 1-18, 2007) (Year: 2007).*
Phiney Stem Cells, 25: 2896-2902, 2007) (Year: 2007).*
Feng (CNS Neuroscience & Therapeutics, 18: 142-148, 2012) (Year: 2012).*
Duncan (Stem Cell Research & Therapy, 8: 1-9, 2017) (Year: 2017).*
Mead (PLoS ONE 6(8): e23244 p. 1-12, 2011) (Year: 2011).*
Vink (J Neuro Res, 96: 527-535, 2018) (Year: 2018).*
Weber (Transl Med (2019) 17:305, p. 1-19, 2019 (Year: 2019).*
Ocansey (J Transl Med, 18(42): 1-14, 2020 (Year: 2020).*

(Continued)

*Primary Examiner* — Anoop K Singh
*Assistant Examiner* — Magdalene K Sgagias
(74) *Attorney, Agent, or Firm* — Workman Nydegger

(57) ABSTRACT

The present invention relates to an adult stem cell line introduced with an HGF gene and a neurogenic transcription factor gene of a bHLH family, a preparation method of the adult stem cell line, a composition for the prevention or treatment of neurological diseases comprising the adult stem cell line, and a method for treating neurological diseases comprising the step of administering the composition to a subject having neurological diseases or suspected of having neurological diseases. The adult stem cells according to the present invention, which are introduced with an HGF gene and a neurogenic transcription factor gene of a bHLH family, can be used to overcome chronic impairment caused by cell death following stroke. Thus, the adult stem cells can be developed as a novel therapeutic agent or widely used in clinical trial and research for cell replacement therapy and gene therapy that are applicable to neurological diseases including Parkinson's disease, Alzheimer disease, and spinal cord injury as well as stroke.

5 Claims, 8 Drawing Sheets
Specification includes a Sequence Listing.

(56) References Cited

OTHER PUBLICATIONS

Ha et al. "Effects of mesenchymal stem cells transfected with human hepatocyte growth factor gene on healing of burn wounds" Chinese Journal of Traumatology (2010) vol. 13, No. 6, pp. 349-355.

Song et al. "Transfection of HGF gene enhances endothelial progenitor cell (EPC) function and improves EPC transplant efficiency for balloon-induced arterial injury in hyperchilesterolemic rats" Vasculat Pharmacology (2009) vol. 51, pp. 205-213.

Human neurogenic basic-helix-loop-helix protein (neuroD3) gene, complete cds (GenBank entry U63842.1), (McMcormick et al), (Dec. 4, 1996).

Kim et al. "Neural Induction with Neurogenin1 Increases the Therapeutic Effects of Mesenchymal Stem Cells in the Ischemic Brain" Stem Cells (2008) vol. 26, pp. 2217-2228.

Savitz et al. "Stem Cell Therapy as an Emerging Paradigm for Stroke (Steps) II" Stroke (2011) vol. 42, pp. 825-829.

Boltze et al., "Stem Cells as an Emerging Paradigm in Stroke 4 Advancing and Accelerating Preclinical Research", Stroke, vol. 50, No. 11, pp. 3299-3306.

Jackson et al. "Adult mesenchymal stem cells: Differentiation potential and therapeutic applications," Journal of Postgraduate Medicine, (2007) vol. 53, Issue 2, pp. 121-127.

Kosztowski, Thomas et al., "Applications of neural and mesenchymal stem cells in the treatment of gliomas", NIH Public Access, National Institute of Health, 9(5), pp. 597-612 (2009).

Lan et al: "Hepatocyte growth factor 1-15 promotes proliferation and migration in immortalized progenitor cells," Neuroreport: An International Journal For The Rapid Communication Of Research In Neuroscience, Lippincott Williams & Wilkins, UK, (2008) vol. 19, No. 7, pp. 765-769.

Mead et al. "Optimised and rapid pre-clinical screening in the SODI transgenic mouse model of amyotrophic lateral sclerosis (ALS)." PLoS One (2011) vol. 6, Issue 8. e23244.

Savitz et al., "Stem Cells as an Emerging Paradigm in Stroke 3 Enhancing the Development of Clinical Trials", Stroke, vol. 45, No. 2, Feb. 2014, pp. 634-639.

Vink, R. "Large animal models of traumatic brain injury," Journal of Neuroscience Research (2017) vol. 96, Issue 4, pp. 527-535.

Weber et al. "Modeling trauma in rats: similarities to humans and potential pitfalls to consider," Journal of Translational Medicine (2019) 17:305, pp. 1-19.

Kim et al (Stem Cells, 26: 2217-2228, 2008 (Year: 2008).

Non-Final Office Action received for U.S. Appl. No. 16/688,434, dated Nov. 16, 2020, 17 pages.

Toshihiko Yamashita, (Research Activities of Sapporo Medical University 2001-2004, edited Committee for International Affairs and Medical Exchanges Sapporo Medical University, p. 1-167, 2005 (Year: 2005).

Final Office Action received for U.S. Appl. No. 16/688,434, dated Apr. 1, 2021, 20 pages.

Final Office Action received for U.S. Appl. No. 16/688,434, dated Jan. 21, 2022, 21 pages.

* cited by examiner

METHOD FOR INTRODUCING HEPATOCYTE GROWTH FACTOR AND NEUROGENIN 1 INTO MESENCHYMAL STEM CELLS

RELATED APPLICATIONS

This application is a US national phase entry under 35 U.S.C. 371 of PCT/KR2012/004082, filed May 23, 2012, which claims the benefit of Korean Application Serial No. 10-2011-0048628, filed May 23, 2011, both of which are incorporated herein by reference, in its entirety.

TECHNICAL FIELD

The present invention relates to an adult stem cell line, modified by introducing a gene encoding a hepatocyte growth factor (HGF) and a gene encoding a neurogenic transcription factor of a basic helix-loop-helix (bHLH) family into an adult stem cell line and uses thereof, and more particularly, to an adult stem cell line introduced with a hepatocyte growth factor gene and a neurogenic transcription factor gene of a basic helix-loop-helix family, a preparation method of the adult stem cell line, a composition for the prevention or treatment of neurological diseases comprising the adult stem cell line, and a method for treating neurological diseases comprising the step of administering the composition to a subject having neurological diseases or suspected of having neurological diseases.

BACKGROUND ART

Mesenchymal stem cell (MSC) are stroma cells that help hematopoiesis in the bone marrow and have the ability to differentiate into a variety of mesodermal lineage cells, including osteocytes, chondrocytes, adipocytes, and myocytes, while also maintaining a pool of undifferentiated stem cells, and thus have gained prominence as a cell source for artificial tissues.

As MSCs have been reported to have a potential to differentiate into neuroglial cells in the brain, it has been proposed that MSCs can be utilized as sources for the treatment of neurological diseases in the central nervous system.

Several growth factors or hormones have been known to induce differentiation of undifferentiated cells into artificial neuronal cells. Unfortunately, those methods have a problem of generating non-neuronal cells together with neuronal cells, and the problem is more pronounced when the cells are transplanted into this brain of experimental animals. Thus, a need has existed to develop a direct method of inducing differentiation of MSCs into neuronal cells.

Neurogenin, also called NeuroD, is as transcription factor belonging to the basic helix-loop-helix (bHLH) family that plays an important role in the formation of the nervous system, and forms a complex with other bHLH proteins such as E12 or E47 to bind to DNA sequences containing the E-box or on rare occasions, DNA sequences containing the N-box. This binding has been found to be critical for bHLH proteins to activate tissue-specific gene expression that promotes neuronal differentiation.

The present inventors have endeavored to develop a stable material that effectively differentiates MSCs into neuronal cells. As a result, they have unexpectedly found that MSCs transduced with bHLH transcription factors such as neurogenin and neuroD can continuously express the bHLH transcription factors; and that the MSCs expressing the bHLH transcription factors can be transdifferentiated into a high level of neuronal cells when transplanted into the brain of experimental animals. On the basis of this finding, they reported that differentiation of MSCs into neuronal cells was induced to obtain excellent therapeutic effects in animal models of stroke, compared with non-induced MSCs (Korean Patent No. 10-0519227).

The use of MSCs in the treatment of neurological diseases is advantageous in that it is possible to use autologous cells rather than heterologous cells. In a practical therapeutic procedure, however, the method has a disadvantage of requiring 2 to 4 weeks for isolation and cultivation of autologous cells and gene transfection, until autologous cell therapy after onset of stroke. Therefore, to address the problem of the time-consuming clinical procedure of autologous cell transplantation after the onset of stroke, many studies have been made to develop a method of verifying and maximizing the therapeutic efficacies of autologous cells on chronic injuries.

HGF, also known as scatter factor, is known to be a heparin-binding glycoprotein that has a strong anti-fibrotic activity in organs such as liver or kidney (Silver et al., Nat. Rev. Neurosci., 5:146-156, 2004). Studies of hepatocyte growth factor for the treatment of neurological diseases including stroke and spinal cord injury are now in progress. Its therapeutic effects on acute diseases have been reported, but a successful outcome on chronic diseases has not been reported yet.

DISCLOSURE OF INVENTION

Technical Problem

The present inventors have made many efforts to develop a therapeutic composition for chronic stroke, comprising MSCs introduced with HGF as an active ingredient. As a result, they found that MSCs introduced with a bHLH transcription factor neurogenin 1 continuously express the bHLH transcription factor, and the MSCs further introduced with HGF showed therapeutic effects when transplanted into animal models of stroke, thereby completing the present invention.

Solution to Problem

An object of the present invention is to provide an adult stem cell line, modified by introducing a gene encoding a hepatocyte growth factor (HGF) and a gene encoding a neurogenic transcription factor of a basic helix-loop-helix (bHLH) family into an adult stem cell line.

Another object of the present invention is to provide a preparation method of the adult stem cell line.

Still another object of the present invention is to provide a composition for the prevention or treatment of neurological diseases comprising the adult stem cell line.

Still another object of the present invention is to provide a method for treating neurological diseases, comprising the step of administering the composition to a subject having neurological diseases or suspected of having neurological diseases.

Advantageous Effects of Invention

The adult stem cells according to the present invention, which are introduced with an HGF gene and a neurogenic transcription factor gene of a bHLH family, can be used to overcome chronic impairment caused by cell death following stroke. Thus, the adult stem cells can be developed as a novel therapeutic agent or widely used in clinical trial and research for cell replacement therapy and gene therapy that are applicable to neurological diseases including Parkinson's disease, Alzheimer disease, and spinal cord injury as well as stroke.

BRIEF DESCRIPTION OF DRAWINGS

FIG. 1 is photographs showing the differentiation of MSCs into adipocytes, chondrocytes, and osteocytes, in which FIG. 1a is a photograph of adipocytes differentiated from MSCs, stained with oil red O, FIG. 1b is a photograph of chondrocytes differentiated from MSCs, stained with alcian blue, and FIGS. 1c and 1d are photographs of osteocytes differentiated from MSCs, stained with alkaline phosphatase and von Kossa, respectively;

BEST MODE FOR CARRYING OUT THE INVENTION

Figure 1:
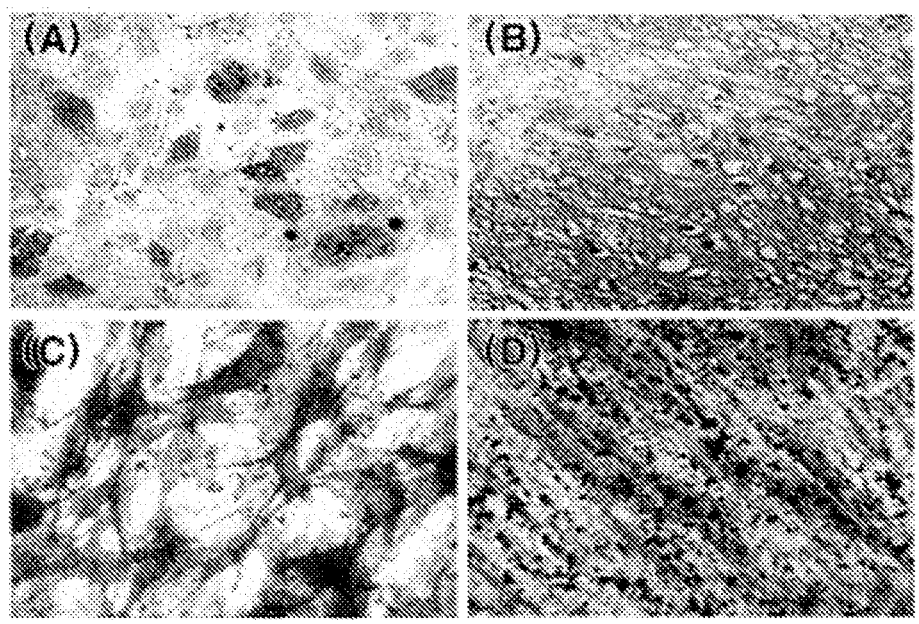

In one aspect of the present invention, the present invention provides An adult stem cell line, modified by introducing a gene encoding a hepatocyte growth factor (HGF) and a gene encoding a neurogenic transcription factor of a basic helix-loop-helix (bHLH) family into an adult stem cell line.

As used herein, the term "adult stem cell" means an undifferentiated cell that can differentiate into specialized cell types of the tissue if needed. The adult stem cell line is, but is not particularly limited to, preferably a stem cell derived from bone marrow, adipose tissue, blood, umbilical cord blood, liver, skin, gastrointestinal tract, placenta, uterus or aborted fetuses, more preferably a bone marrow-derived adult stem cell line, and most preferably a bone marrow-derived MSC. The bone marrow-derived adult stem cell includes a variety of adult stem cells such as MSCs and hematopoietic stem cells capable of producing blood cells and lymphocytes. Among them, MSCs are able to easily proliferate ex vivo and differentiate into a variety of cell types (adipocytes, chondrocytes, myocytes, and osteocytes). Thus, they can be used as a useful target in gene and cell therapy, but the use thereof is not particularly limited.

As used herein, the term "Hepatocyte Growth Factor (HGF)", also known as scatter factor, means a multifunctional heterodimeric polypeptide produced by mesenchymal cells. The HGF is composed of a 69 kDa alpha-chain containing the N-terminal finger domain and four Kringle domains, and a 34 kDa beta-chain which has a similarity to protease domains of chymotrypsin-like serine protease. Human HGF is synthesized as a biologically inactive single chain precursor consisting of 728 amino acids. Biologically active HGF is achieved through cleavage at the R494 residue by a specific serum serine protease. The active HGF is a heterodimer which is composed of 69 kDa alpha-chain and 34 kDa beta-chain linked via a disulfide bond. In the present invention, the HGF is introduced into the adult stem cell line to obtain a transformed cell line. A nucleotide sequence encoding the preferred HGF is known (GenBank Accession No. NM_000601.4 166-2352, or BC130286.1 (76-2262)).

As used herein, the term "Basic Helix-Loop-Helix (bHLH)" expresses the shape of transcription factors, and refers to a form of two helices connected by a loop. The bHLH transcription factors are known to play important roles in gene expression of multi-cellular organisms.

The bHLH transcription factors are, but are not particularly limited to, preferably neurogenic transcription factors, and more preferably neurogenin 1 gene (GenBank Accession No: U63842, U67776), neurogenin 2 gene (GenBank Accession No: U76207, AF303001), neuro D1 gene (GenBank Accession No: U24679, AB018693), MASH1 gene (GenBank Accession No: M95603, L08424), MATH3 gene (GenBank Accession No: D85845), E47 gene (GenBank Accession No: M65214, AF352579) or the like. Moreover, the neurogenic transcription factor having an alteration, a deletion, or a substitution in a part of the polynucleotide sequence may be used, as long as it shows an activity equivalent or similar to that of the neurogenic transcription factor.

Figure 3:
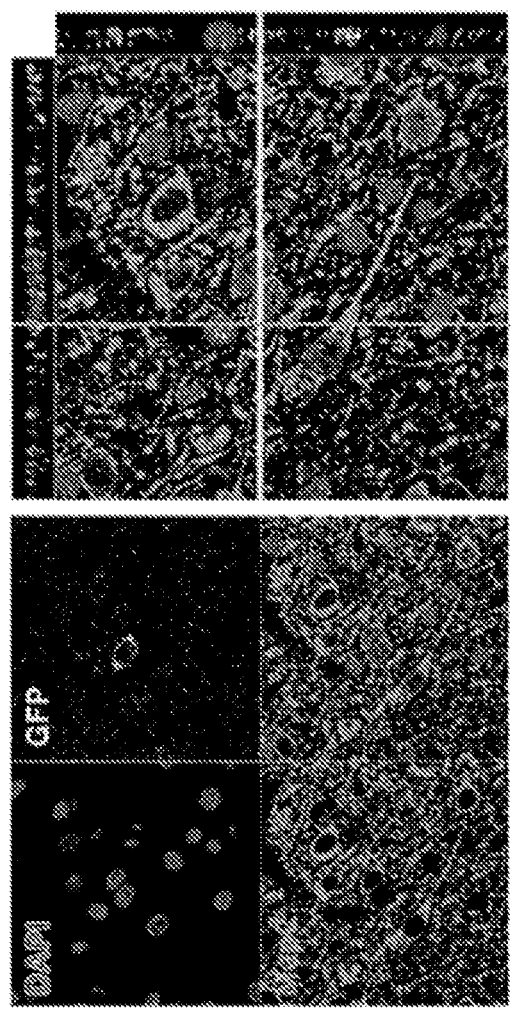
FIG. 3 is the result of immunohistochemical staining using anti-neuronal marker TuJ1 (Beta-Tubulin-III) antibody to examine neurogenic differentiation of MSCs at two weeks after the human neurogenin 1 gene-introduced MSCs were infected with GFP-expressing adenovirus and transplanted into the striatum of albino rat.

The MSCs introduced with the bHLH transcription factor gene have the potential to differentiate into neuronal cells rather than the potential to differentiate into osteocytes, myocytes, adipocytes, and chondrocytes, and they are able to differentiate into neuronal cells under particular conditions in vitro. According to one Example of the present invention, adult stem cells introduced with the HGF gene and neurogenin 1 gene were prepared, and they were found to effectively differentiate into neuronal cells when transplanted into the brain tissue of experimental animals (FIG. 3).

As used herein, the term "adult stem cell line introduced with the HGF gene and the neurogenic transcription factor gene of the bHLH family" refers to an adult stem cell line that is introduced with the above described HGF gene and neurogenic transcription factor gene of the bHLH family, preferably an adult stem cell line that is introduced with the HGF gene of SEQ ID NO. 1 and the neurogenin 1 gene of SEQ ID NO. 2. However, the adult stem cell line is not particularly limited thereto, as long as it retains the ability to differentiate into neuronal cells.

With respect to the objects of the present invention, it is preferable that the HGF gene is cloned into a vector, and then introduced into the adult stem cell.

As used herein, the term "vector", which describes an expression vector capable of expressing a target protein in a suitable host cell, refers to a genetic construct that includes essential regulatory elements to which a gene insert is operably linked in such a manner as to be expressed.

As used herein, the term "operably linked" refers to a functional linkage between a nucleic acid sequence coding for the desired protein and a nucleic acid expression control sequence in such a manner as to allow general functions. The operable linkage may be prepared using a genetic recombinant technique that is well known in the art, and site-specific DNA cleavage and ligation may be carried out using enzymes that are generally known in the art.

The vector is, but is not particularly limited to, preferably a plasmid vector, a cosmid vector, a viral vector, and more preferably, viral vectors derived from HIV (Human immunodeficiency virus), MLV (Murine leukemia virus), ASLV (Avian sarcoma/leukosis), SNV (Spleen necrosis virus), RSV (Rous sarcoma virus), MMTV (Mouse mammary tumor virus), MSV (Murine sarcoma virus), adenovirus, adeno-associated virus, herpes simplex virus or the like.

Figure 2:
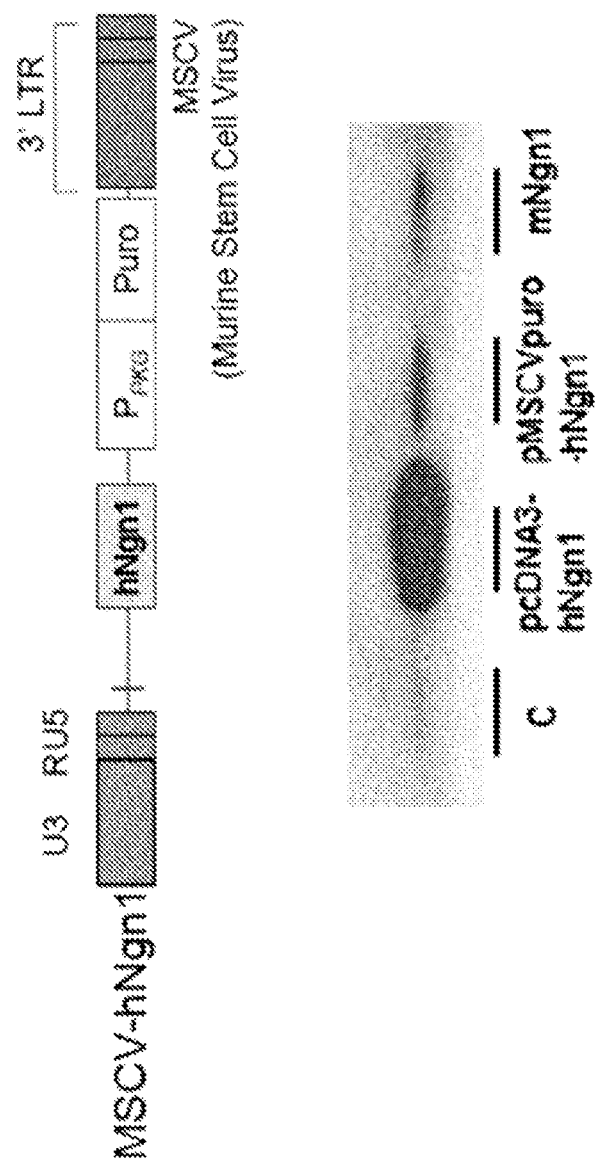
FIG. 2 is the result of Western blotting (lower panel) showing the expression of human neurogenin 1 in 293T cells that were introduced with a retroviral vector (upper panel) containing human neurogenin 1 gene.

According to one Example of the present invention, for the introduction of neurogenin 1 gene, the coding region (55-768 bp) in the gene sequence of GenBank Accession No. U63842 of FIG. 2 was cloned into a pMSCV-puro plasmid to prepare a recombinant vector pMSCV/puro-hNgn1, and the obtained recombinant vector was introduced into a cell line producing retrovirus to prepare a retroviral vector. Then, the obtained retroviral vector was introduced into a bone marrow-derived MSC line to prepare a transformed adult stem cell.

According to another Example of the present invention, for the introduction of HGF gene, the coding region (166-2352 bp) in the gene sequence of GenBank Accession No. NM_000601.4 was cloned into pShuttle-CMV, and then a recombinant vector pAd-HGF was prepared by recombination with pAdEasy-1. The recombinant vector was linearized by cleavage with the restriction enzyme Pad, and the linearized recombinant vector was introduced into a cell line producing adenovirus to prepare an Adeno-HGF vector. Then, the obtained Adeno-HGF vector was introduced into a bone marrow-derived MSC line to prepare a transformed adult stem cell.

The gene introduction into the adult stem cell of the present invention is, but is not particularly limited to, performed by transformation, and the transformation may be readily performed by the typical method known in the art.

As used herein, the term "transformation" refers to artificial genetic alteration by introduction of a foreign DNA or a foreign DNA-containing viral vector into a host cell, either as an extrachromosomal element, or by chromosomal integration. Generally, the transformation method includes infection using retrovirus and adenovirus, $CaCl_2$ precipitation of DNA, a Hanahan method that is an improved $CaCl_2$ method by using dimethylsulfoxide (DMSO) as a reducing material, electroporation, calcium phosphate precipitation, protoplastfusion, agitation using silicon carbide fiber, Agrobacterium-mediated transformation, PEG-, dextransulfate-, lipofectamine-, and desiccation/inhibition-mediated transformation. According to one example of the present invention, transformation was performed by introduction of the retroviral vector containing neurogenin and the Adeno-HGF vector containing HGF gene into stem cells.

In another aspect, the present invention provides a preparation method of the adult stem cell line that is introduced with the HGF gene and the neurogenic 1 gene.

As described above, the type of the adult stem cell line introduced with the HGF gene and the neurogenic 1 gene is not particularly limited, and any cell line may be used as the cell line of the present invention, as long as it has the potential to differentiate into the specialized cell types of the tissue.

Preferably, the adult stem cell line may be an adult stem cell line derived from bone marrow, adipose tissue, blood, umbilical cord blood, liver, skin, gastrointestinal tract, placenta, uterus or aborted fetuses. More preferably, the adult stem cell line is a bone marrow-derived adult stem cell line. Much more preferably, the adult stem cell line is a bone marrow-derived MSC line.

Introduction of a particular gene into a stem cell line may be performed by using a transformation method. As described above, a typical transformation method known in the art may be used without limitation. According to one Example of the present invention, a transformed adult stem cell line was prepared by introduction of the MSCV-puro/hNgn1 and Adeno-HGF into the adult stem cell line. After transfection of MSCs with the MSCV-puro/hNgn1 gene, puromycin was used for selection. After transfection of MSCs with Adeno-HGF, an HGF antibody was used to examine its expression, and multiplicity of infection (MOI) was determined and used.

The method of producing the bone marrow-derived adult stem cell line introduced with HGF gene and neurogenin 1 gene of the present invention may include the following steps:

(a) introducing a gene coding hepatocyte growth factor having a nucleotide sequence of SEQ ID NO. 1 and a gene coding neurogenin 1 having a nucleotide sequence of SEQ ID NO. 2 into cultured adult stem cells;

(b) selecting the modified adult stem cell line that is introduced with both genes coding hepatocyte growth factor and neurogenin 1; and (c) culturing the selected the modified adult stem cell line.

In the method of producing the bone marrow-derived adult stem cell line that is introduced with HGF gene and neurogenin 1 gene, introducing the gene coding hepatocyte growth factor and the gene coding neurogenin 1 are performed sequentially or in reverse order, or simultaneously, but the order and method are not particularly limited.

According to one Example of the present invention, among the adult stem cells, bone marrow-derived MSCs were isolated. The isolated MSCs were cultured in a DMEM medium containing 10% FBS, 10 ng/mL bFGF, and 1% penicillin/streptomycin, and subcultured up to four passages for use in experiments.

In the step of transforming with the neurogenin 1 gene, the neurogenin 1 gene was ligated to the pMSCV-puro vector using T4 DNA ligase, and transformed into $E.\ coli$ DH5α. Finally, a pMSCV-puro/hNgn1 vector was prepared by insertion of hNgn1 gene into the pMSCV-puro vector, and the neurogenin 1 gene was introduced into the subcultured cell line. The cells introduced with neurogenin 1 were subcultured in the medium containing 2 μg/mL of puromycin for 2 weeks so as to select the surviving cells introduced with neurogenin 1. Finally, a cell line continuously expressing neurogenin 1 was prepared by the above procedure.

In the step of transforming with the HGF gene, the HGF-cloned pShuttle-CMV-HGF and pAdEasy-1 were co-transformed into *E. coli* (BJ 5183 strain) by electroporation, and then cultured in a medium containing kanamycin (50 μg/mL) until colonies were formed. Plasmids were obtained from each colony, and candidate colonies were selected by standard restriction enzyme digestion. Base sequence was analyzed to obtain pAd-HGF. The pAd-HGF was linearized by cleavage with the restriction enzyme PacI, and introduced into HEK293 cell by $CaCl_2$ precipitation to obtain a culture broth containing Adeno-HGF virus. In order to select a MSC line where HGF was successfully introduced, protein expression of HGF was examined by immunocytochemical staining using an antibody against HGF.

In still another aspect, the present invention provides a composition for the prevention or treatment of neurological diseases, comprising the adult stem cell line introduced with HGF gene and neurogenin 1 gene.

As used herein, the term "neurological diseases" refers to a variety of diseases associated with nerves, in particular, cranial nerves. The neurological diseases may be, but are not particularly limited to, Parkinson's disease, Alzheimer disease, Huntington's chorea, amyotrophic lateral sclerosis, epilepsy, schizophrenia, acute stroke, chronic stroke, or spinal cord injury, and preferably chronic stroke.

As used herein, the term "prevention" refers to all of the actions in which the occurrence of neurological diseases or diseases associated therewith is restrained or retarded by using the adult stem cell line introduced with HGF gene and neurogenin 1 gene.

As used herein, the term "treatment" refers to all of the actions in which the symptoms of neurological diseases or diseases associated therewith have taken a turn for the better or been modified favorably by using the adult stem cell line introduced with HGF gene and neurogenin 1 gene.

The MSCs introduced with HGF gene and neurogenin 1 gene of the present invention may exist in a form of a pharmaceutical composition including the MSCs for treatment.

Meanwhile, the composition of the present invention may be a pharmaceutical composition further including a pharmaceutically acceptable carrier. The composition including a pharmaceutically acceptable carrier may be prepared into oral or parenteral formulation. Formulations may be prepared using diluents or excipients ordinarily employed, such as a filler, an extender, a binder, a wetting agent, a disintegrating agent, and a surfactant. Examples of the solid preparation for oral administration include a tablet, a pill, a powder, a granule, and a capsule, and the solid preparation may be prepared by mixing one or more compounds with at least one excipient such as starch, calcium carbonate, sucrose, lactose, and gelatin. Further, in addition to the excipients, lubricants such as magnesium stearate and talc may be used. Examples of a liquid preparation for oral administration include a suspension, a liquid for internal use, an emulsion, and a syrup, and various excipients such as a wetting agent, a sweetener, a flavor, and a preservative may be contained, in addition to general diluents such as water and liquid paraffin. Examples of the preparation for parenteral administration may include an aseptic aqueous solution, a non-aqueous solvent, a suspension, an emulsion, a lyophilized agent, and suppository. As the non-aqueous solvent and suspension, propylene glycol, polyethylene glycol, plant oil such as olive oil, and injectable ester such as ethyloleate may be used. As a suppository base, witepsol, macrogol, tween 61, cacao butter, lauric butter, glycerogelatin or the like may be used. The pharmaceutical composition may be formulated into any preparation selected from the group consisting of a tablet, a pill, a powder, a granule, and a capsule, a suspension, a liquid for internal use, an emulsion, and a syrup, an aseptic aqueous solution, a non-aqueous solvent, a suspension, an emulsion, a lyophilized agent, and suppository.

In still another aspect, the present invention provides a method for treating neurological diseases, comprising the step of administering the composition to a subject having neurological diseases or suspected of having neurological diseases.

As used herein, the term "subject" refers to living organisms that have the nervous system and thus are susceptible to the above described neurological diseases caused by various factors, and preferably mammals.

As used herein, the term "mammal" refers to mouse, rat, rabbit, dog, cat, and especially human, and refers to any organism of the Class "Mammalia" of higher vertebrates that nourish their young with milk secreted by mammary glands.

The composition of the present invention may be administered to a subject via any of the common routes, as long as it is able to reach a desired tissue. A variety of administration modes are contemplated, including intraperitoneally, intravenously, intramuscularly, subcutaneously, intradermally, orally, intranasally, intrapulmonarily and intrarectally, but the present invention is not limited to these exemplified administration modes. In addition, the composition of the present invention may be used singly or in combination with hormone therapy, drug therapy and biological response regulators in order to exhibit antioxidant effects.

Moreover, the composition of the present invention may be administered in a pharmaceutically effective amount. As used herein, the term "pharmaceutically effective amount" refers to an amount sufficient for the treatment of diseases, which is commensurate with a reasonable benefit/risk ratio applicable for medical treatment. An effective dosage of the present composition may be determined depending on the subject and severity of the diseases, age, gender, drug activity, drug sensitivity, administration time, administration route, excretion rate, duration of treatment, simultaneously used drugs, and other factors known in medicine. The composition of the present invention may be administered as a sole therapeutic agent or in combination with other therapeutic agents, and may be administered sequentially or simultaneously with conventional therapeutic agents. This administration may be provided in single or multiple doses. Taking all factors into consideration, it is important to conduct administration of minimal doses capable of giving the greatest effects with no adverse effects, such doses being readily determined by those skilled in the art.

In addition, the composition of the present invention may be used singly or in combination with surgical operation, hormone therapy, drug therapy and biological response regulators in order to prevent or treat inflammatory diseases.

MODE FOR THE INVENTION

Hereinafter, the present invention will be described in more detail with reference to Examples. However, these Examples are for illustrative purposes only, and the invention is not intended to be limited by these Examples.

Example 1: Isolation and Culture of MSCs

Example 1-1: Isolation of MSCs 4 mL of HISTOPAQUE 1077(Sigma) and 4 mL of bone marrow obtained from Bone marrow bank (Korean Marrow Donor Program, KMDP) were added to a sterilized 15 mL test-tube, and centrifugation was performed using a centrifuge at room temperature and 400×g for 30 minutes. After centrifugation, 0.5 mL of the buffy coat located in the interphase was carefully collected using a pasteur pipette, and transferred into a test-tube containing 10 mL of sterilized phosphate buffered saline (PBS). The transferred buffy coat was centrifuged at 250×g for 10 minutes to remove the supernatant and 10 mL of phosphate buffer was added thereto to obtain a suspension, which was centrifuged at 250×g for 10 minutes.

The above procedure was repeated twice and a DMEM medium (Gibco) containing 10% FBS (Gibco) was added to the resulting precipitate. A portion of the resulting solution corresponding to $1 \times 10^7$ cells was placed in a 100 mm dish and incubated at 37° C. for 4 hours while supplying 5% $CO_2$ and 95% air. The supernatant was then removed to eliminate cells that were not attached to the bottom of the culture dish, and a new medium was added to continue culturing.

Example 1-2: Culture of MSCs

The MSCs isolated in Example 1-1 were incubated in a $CO_2$ incubator kept at 37° C., while changing an MSC medium (10% FBS+10 ng/mL of bFGF (Sigma)+1% penicillin/streptomycin (Gibco)+89% DMEM) at an interval of 2 days. When the cells reached approximately 80% confluence, the cells were collected using 0.25% trypsin/0.1 mM EDTA (GIBCO) and diluted 20 fold with the medium, and then subcultured in the new dishes. The rest of cells thus obtained were kept frozen in a medium containing 10% DMSO, and their potentials to differentiate into adipocytes, chondrocytes, and osteocytes were examined as follows.

Example 1-3: Adipogenic Differentiation

MSCs were cultured in the MSC medium for a predetermined period of time, followed by culturing in an adipogenic differentiation induction medium (DMEM medium containing 1 μM dexamethasone (Sigma), 0.5 μM methylisobutylxanthine (Sigma), 10 μg/mL of insulin (GIBCO), 100 nM indomethacin (Sigma) and 10% FBS) for 48 hours. The resulting mixture was subsequently incubated in an adipogenic maintenance medium (DMEM medium containing 10 μg/mL of insulin and 10% FBS) for 1 week and stained with oil red O (FIG. 1a). FIG. 1a is a photograph of adipocytes differentiated from MSCs, which were stained with oil red O. As shown in FIG. 1a, lipid droplets stained with red were observed inside the cells, indicating that MSCs were successfully differentiated into adipocytes.

Example 1-4: Chondrogenic Differentiation

MSCs were cultured in the MSC medium for a predetermined period of time, and $2 \times 10^5$ of the cells were collected using trypsin and transferred into a test-tube, centrifuged, and then, re-incubated in 0.5 mL of a serum-free chondrogenic differentiation induction medium (50 mL of high-glucose DMEM (GIBCO), 0.5 mL of 100×ITS (0.5 mg/mL of bovine insulin, 0.5 mg/mL of human transferrin, 0.5 mg/mL of sodium selenate (Sigma), 50 μL linolenic acid-albumin (Sigma), 0.2 mM 100 nM dexamethasone, and 10 ng/mL of TGF-beta1 (Sigma)) for 3 weeks while replacing the medium every 3 days. Then, the cells were fixed with 4% paraformaldehyde, sectioned using a microtome, and then stained with alcian blue (FIG. 1b). FIG. 1b is a photograph of chondrocytes differentiated from MSCs, which were stained with alcian blue. As shown in FIG. 1b, the extracellular cartilage matrix was stained blue and the presence of chondrocytes in cartilage lacunae was observed, indicating that the MSCs were differentiated into chondrocytes.

Example 1-5: Osteogenic Differentiation

MSCs were cultured in the MSC medium for a predetermined period of time, followed by culturing in an osteogenic differentiation induction medium (DMEM containing 10 mM beta-glycerol phosphate (Sigma), 0.2 mM ascorvate-2-phosphate (Sigma), 10 nM dexamethasone and 10% FBS) for 2 weeks while replacing the medium every 3 days. Then, the cells were fixed with paraformaldehyde, and stained with von Kossa and alkaline phosphatase (AP) (FIGS. 1c and 1d). FIGS. 1c and 1d are photographs of osteocytes differentiated from MSCs, which were stained with alkaline phosphatase and von Kossa, respectively. As shown in FIGS. 1c and 1d, the extracellular accumulation of calcium minerals in the form of hydroxyapatite and the increase of the intracellular alkaline phosphatase activity suggest that the MSCs were differentiated into osteocytes.

Example 2: Construction and Expression of Retrovirus of Human Neurogenic Transcription Factor, Neurogenin 1

Example 2-1: Construction of Retroviral Vector Expressing Human Neurogenin 1

The sequence of SEQ ID NO. 2 corresponding to the coding region (55-768 bp) in the U63842 gene sequence was ligated into a pMSCV-puro vector (Clontech) using T4 DNA ligase (Roche), and then transformed into *E. coli* DH5α to finally construct a pMSCV-puro/hNgn1 vector where human neurogenin 1 (hNgn1) gene was inserted into the pMSCV-puro vector. The constructed pMSCV-puro/hNgn1 vector was introduced into 293T cells by calcium phosphate precipitation, and the expression was examined by Western blotting (FIG. 2). FIG. 2 is the result of Western blotting (lower panel) showing the expression of hNgn1 in 293T cells that was introduced with a retroviral vector (upper panel) containing hNgn1 gene.

Example 2-2: Preparation of Retrovirus Containing Neurogenin 1

The pMSCV-puro/hNgn1 vector was introduced into a retroviral packaging cell, PA317 (ATCC CRL-9078) or PG13 (ATCC CRL-10686) according to the calcium phosphate precipitation method. After 48 hours, the culture solution was collected and filtered with 0.45 μm membrane to obtain retrovirus solution. The retrovirus solution was kept at −70° C. until use.

Example 3: Construction of Neurogenin 1 Gene-Introduced MSCs and In Vivo Neuronal Differentiation

Example 3-1: Introduction of Neurogenin 1 into MSCs

MSCs were cultured to 70% confluence in 100 mm culture dishes. Added thereto was 4 mL of the neurogenin 1 retrovirus solution obtained in Example 2-2 which was mixed with polybrene (Sigma) to a final concentration of 8 μg/mL, and incubated for 8 hours. The retrovirus solution was then removed, and the MSCs were cultured in 10 mL of MSC medium for 24 hours, followed by re-infection of the retrovirus. The above procedure was repeated 1-4 times. Then, MSCs were collected using trypsin and diluted 20 fold with the medium. The obtained cells were subcultured in a medium supplemented with 2 µg/mL of puromycin (Sigma) for 2 weeks so as to select the surviving cells infected with retrovirus. Finally, MSCs having a puromycin resistance were used as neurogenin 1-expressing cells.

Example 3-2: Labeling of Cells for Transplantation

In order to examine whether neurogenin 1 gene increases the transplantation rate and neuronal differentiation, MSCs introduced with hNgn1 gene were infected with GFP-expressing adenovirus.

The adenovirus transfection was carried out by adding the adenovirus solution having a titer of $1\times10^8$ PFU/mL with 100 MOI already described earlier for 3 hours. After adenovirus transfection, neurogenin 1-introduced MSCs were collected using 0.25% trypsin/0.1% EDTA and diluted with PBS to $3\times10^3$ cells per 1 µL.

Example 3-3: Transplantation

Transplantation was carried out using adult Sprague-Dawley albino female rats (250 g) (Dae Han Bio Link Co., Ltd) as follows:

Firstly, albino rats were anesthetized with an intraperitoneal injection of 75 mg/kg ketamine and 5 mg/kg rumpun, the fur at the incision region was removed, and then the ears and mouth were fixed to a stereotaxic frame. The vertex was sterilized with 70% ethanol and an approximately 1 cm incision was made. Subsequently, 1 µL of PBS containing $3\times10^3$ of hNgn1-expresing MSC (MSC/hNgn1) was put in a 10 µL Hamilton syringe, which was placed in a Hamilton syringe rack. After drilling at the exposed dura at positions of bregma AP, +1.0; ML 3.0; LV, +4.0, 1 µL of the cells was injected at a rate of 0.2 µL/min using a Hamilton syringe. Twenty minutes after injection, the syringe was slowly removed. The incision was sutured using a sterilized thread and needle, and disinfected using a disinfectant. 5 mg/kg of an immunosuppressant cyclosporin A (Sigma) was daily administered by intraperitoneal injection until the brain was extracted.

Example 3-4: Preparation of Tissue Slice

Two weeks after transplantation, the albino rats were anesthetized with an intraperitoneal injection of 75 mg/kg ketamine and 5 mg/kg rumpun. The chests were opened, and perfusion wash-out was performed using saline through the left ventricle. Perfusion fixation was performed using paraformaldehyde in 0.1 M phosphate buffer solution (pH 7.4). The brains were extracted, and post-fixed in the same fixation solution at 4° C. for 16 hours. The post-fixed brain was deposited in 30% sucrose for 24 hours and sectioned using a sliding microtome with a thickness of 35 µm. The sections thus obtained were mounted to silane-coated slides (MUTO PUREW CHEMICAS CO., LTD, Japan) and stored at 4° C. in PBS until use. The tissue sections mounted on slides were dipped in 1×PBS/0.1% Triton X-100 for 30 minutes.

Example 3-5: Immunohistochemistry

Firstly, to block non-specific interaction, the tissue section was reacted with 10% normal horse serum (NHS) at room temperature for 1 hour, and then reacted at 4° C. for 16 hours with primary antibodies of MAP2 (Microtubule-associated protein-2) antibody and GFP antibody each diluted at 1:200. After washing three times with 1×PBS/0.1% Triton X-100 for 15 minutes, the sections were allowed to react with FITC-conjugated anti-mouse IgG (Vector, 1:200) to detect the GFP primary antibody or Taxas red-conjugated anti-mouse IgG (Vector, 1:200) to detect the MAP2 primary antibody (FIG. 3). FIG. 3 is the result of immunohistochemistry using anti-neuronal marker TuJ1 (Beta-Tubulin-III) antibody to examine neurogenic differentiation of MSCs at two weeks after the hNgn1 gene-introduced MSCs were infected with GFP-expressing adenovirus and transplanted into the striatum of albino rat. As shown in FIG. 3, the GFP-expressing cells and the MAP2-expressing cells were overlapped, indicating that neurogenin 1 gene-introduced MSCs were differentiated into neuronal cells.

Example 4: Construction and Expression of HGF Gene-Introduced Adenoviral Vector

Example 4-1: Construction of Adenoviral Vector Expressing HGF

The base sequence of SEQ ID NO. 1 corresponding to the coding region (166-2352 bp) in the gene sequence of GenBank Accession No. NM_000601.4 was introduced into a pShuttle-CMV vector to prepare a pShuttle-CMV-HGF. This vector and pAdEasy-1 were co-transformed into E. coli (BJ 5183 strain) by electroporation, and cultured in a medium containing kanamycin (50 µg/mL) until colonies were formed. Plasmids were obtained from each colony, and candidate colonies were selected by standard restriction enzyme digestion. The base sequence was analyzed to obtain a pAd-HGF vector having HGF. The pAd-HGF was linearized by cleavage with the restriction enzyme Pad, and introduced into HEK293 cell by $CaCl_2$ precipitation to obtain a culture broth containing Adeno-HGF virus.

Example 4-2: Western Blot Analysis on HGF Expression in Adenovirus

Figure 4:
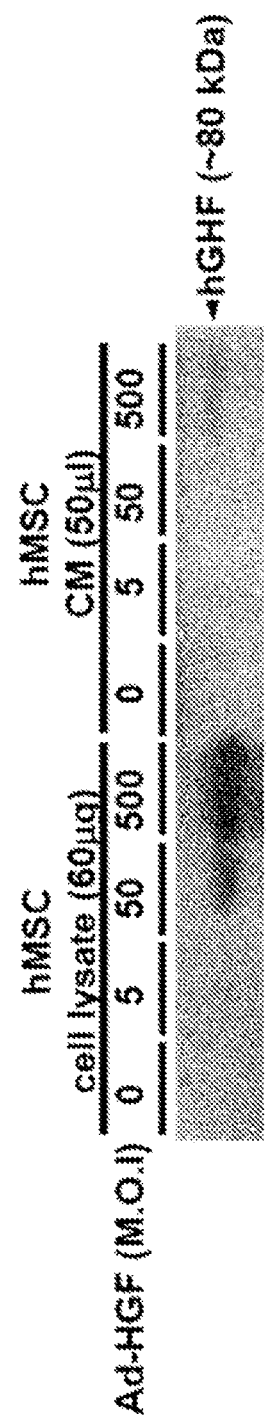
FIG. 4 is the result of Western blot analysis showing the expression of intra-cellular (cell lysate) and extracellular (conditioned-medium; CM) HGF in MSCs introduced with adenoviral vector expressing human HGF.

In order to examine whether HGF was normally expressed in the adenovirus introduced with HGF gene, MSCs were infected with the adenovirus at various concentrations for 2 hours, and the produced HGF was analyzed at intracellular protein (cell lysate) and extracellular protein (conditioned-medium; CM) levels by Western blotting (FIG. 4). FIG. 4 is the result of Western blot analysis showing the expression of intracellular (cell lysate) and extracellular (conditioned-medium; CM) HGF in MSCs introduced with an adenoviral vector expressing human HGF. As shown in FIG. 4, the intracellular HGF was produced in proportion to the concentration of HGF-expressing adenovirus infected into MSCs.

Example 4-3: Immunocytochemistry of Adenovirus-Mediated HGF Expression

Immunocytochemistry was performed in order to examine the intracellular expression of HGF. MSCs were infected with adenovirus expressing HGF at various concentrations, fixed with 4% formalin for 10 minutes, and reacted with 10% normal goat serum (NGS) at room temperature for 1 hour to block non-specific interaction. HGF antibody diluted at 1:200 was used as a primary antibody, and reacted at 4° C. for 16 hours, followed by washing with 1×PBS/0.1%

Figure 5:
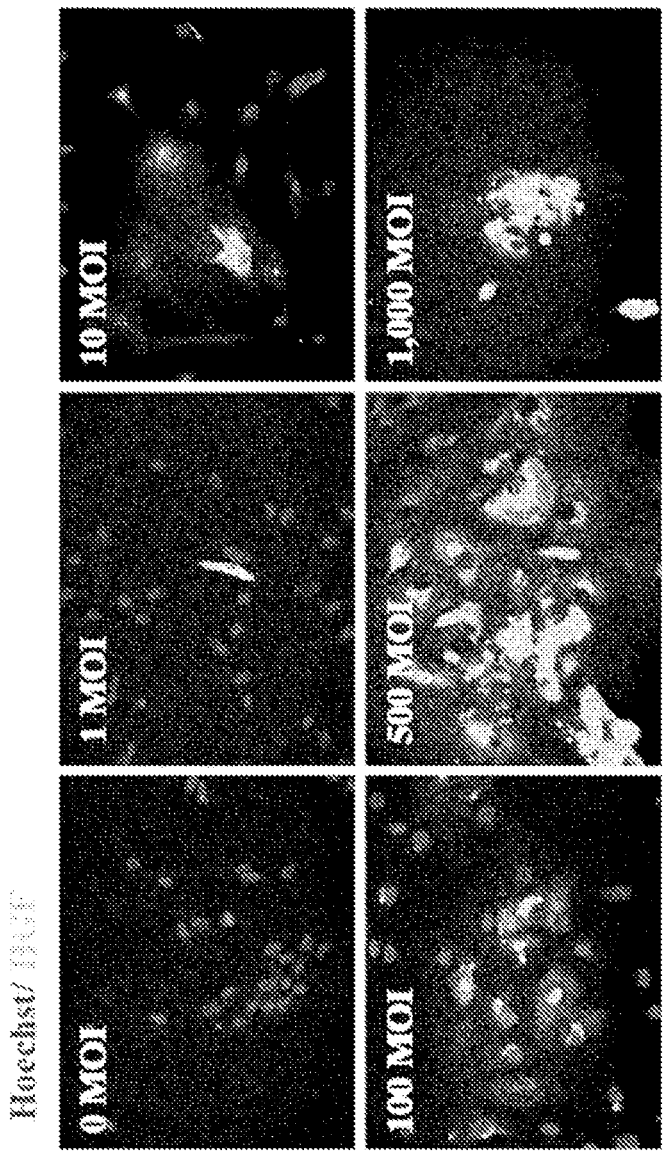
FIG. 5 is a photograph showing the result of immunocytochemistry to examine the expression level of HGF in MSCs that were introduced with serially diluted adenoviral vector expressing human HGF.

Triton X-100 for 15 minutes three times. To detect the HGF primary antibody, the cells were stained with Alexa 488-conjugated mouse Ig-G secondary antibody (Invitrogen) diluted at 1:250, and the nuclei were simultaneously stained with Hoechst (FIG. 5). FIG. 5 is a photograph showing the result of immunocytochemistry to examine the expression level of HGF in MSCs that were introduced with serially diluted adenoviral vector expressing human HGF. As shown in FIG. 5, the intracellular HGF was produced in proportion to the concentration of HGF-expressing adenovirus infected into MSCs.

Example 5: Introduction of HGF Gene into Human Neurogenin 1 Gene-Introduced MSCs and Transplantation Thereof into Stroke Animal Model Example 5-1: Introduction of HGF Gene into hNgn1 Gene-Introduced MSCs hNgn1 gene-introduced MSCs were cultured, until the cells reached to approximately 70% confluence in a 100 mm culture plate. The transfection was carried out by adding HGF-expressing adenovirus solution obtained in Example 4 with 50 MOI for 2 hours. The MSCs were washed with PBS three times, and then MSCs were detached from the culture plate using trypsin.

Example 5-2: Preparation of Stroke Animal Model

Adult male SD-rats weighing 200 g to 250 g were anesthetized with 5% isofluran gas containing 70% $N_2O$ and 30% $O_2$. The right common carotid artery (CCA), right external carotid artery (ECA), and right internal carotid artery (ICA) were exposed through a ventral midline incision in the neck, and approximately 20 mm to 22 mm of 4-0 nylon suture was inserted from CCA to ICA to occlude the right middle cerebral artery (MCA). After 120 minutes, the nylon suture was removed. During the operation, the body temperature of the rats was maintained at 37.8° C., and all surgical instruments were sterilized before use.

Example 5-3: Transplantation of HGF Gene and hNgn1 Gene-Introduced MSCs into Stroke Animal Model 4 weeks after stroke induction, albino rats were placed in a stereotaxic apparatus, and $5.0 \times 10^5$ of HGF gene and hNgn1 gene-introduced MSCs were transplanted at a rate of 0.5 μL/min at positions of bregma AP=+0.5 mm, ML=3.5 mm, DV=5.0 mm and AP=−1.0 mm. ML=3.0, DV=2.5 mm using a 25-Gauge Hamilton syringe.

Five minutes after transplantation, the Hamilton syringe was removed. In addition to the MSCs expressing HGF gene and hNgn1 gene, normal MSCs, normal MSCs introduced with HGF gene, MSCs introduced with hNgn1, and PBS were used for cell transplantation.

Example 6: Introduction of HGF Gene into Human Neurogenin 1 Gene-Introduced MSCs and Evaluation of Their Effectiveness in Stroke Animal Model Example 6-1: Criteria Establishment for Evaluation of Effectiveness of MSC in Stroke Animal Model To evaluate the effectiveness of MSCs transplanted into animals with brain injury, an MRI and behavioral tests were performed. Stroke was induced in albino rats by middle cerebral artery occlusion. After 4 weeks, 3.0T MRI and the behavioral tests were performed to select animals with uniform brain injury, and MSCs introduced with HGF gene and hNgn1 gene were transplanted thereto.

The albino rats were anesthetized with an intraperitoneal injection of 75 mg/kg ketamine and 5 mg/kg rumpun, and an MRI scan of the rat brain was performed using a 3.0T MRI scanner equipped with a gradient system capable of 35 millitesla/m. A fast-spin echo imaging sequence was used to acquire T2-weighted anatomical images, using the following parameters: repetition time, 4,000 ms; effective echo time, 96 ms; field of view, $55 \times 55$ mm$^2$; image matrix, $256 \times 256$; slice thickness, 1.5 mm; flip angle, 90°; number of excitations, 2; pixel size, $0.21 \times 0.21$ mm$^2$.

For the animal behavioral test, Adhesive Removal Test and Rotarod Test were performed. For the Adhesive Removal Tests, an adhesive tape of 10 mm×10 mm was placed on the dorsal paw of each forelimb, and the time to remove each tape from the dorsal paw was measured. For the Rotarod Test, experimental animals were tested for their ability to run on a rotating cylinder that was accelerated from 4 to 40 rpm for 5 minutes. Two weeks before stroke induction, only animals capable of removing the adhesive tape within 10 seconds and remaining on the Rota-rod cylinder for more than 300 seconds were selected and included in the experiment.

Figure 6:
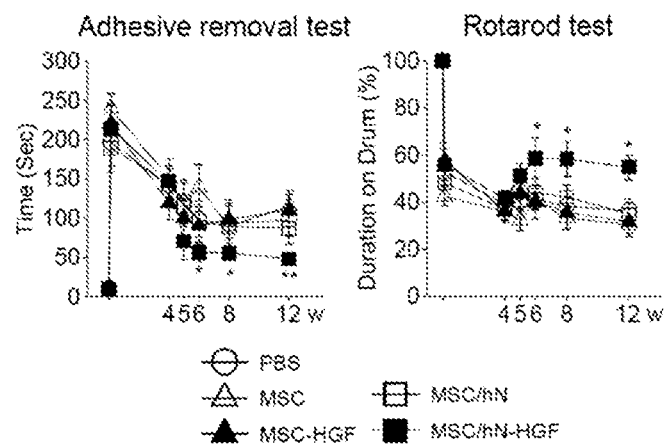
FIG. 6 is graphs showing the results of animal behavioral tests including Adhesive Removal Test (left panel) and Rotarod Test (right panel) to evaluate the therapeutic efficacy of human HGF gene and human neurogenin 1 gene-introduced MSCs in stroke animal model.

Example 6-2: Evaluation on Therapeutic Effectiveness of HGF Gene and hNgn1 Gene-Introduced MSCs in Stroke Animal Model Four weeks after stroke induction, the behavioral tests and MRI were performed to select animals with uniform brain injury. The stroke animal models were transplanted with total 5 cell groups, including a control group PBS, normal MSCs, HGF gene-introduced normal MSCs, and hNgn1-introduced MSCs, as well as the HGF gene and hNgn1 gene-introduced MSCs. The effectiveness of the MSCs in stroke animal model was evaluated based on the behavioral tests and MRI (FIG. 6). FIG. 6 is graphs showing the results of animal behavioral tests of Adhesive Removal Test (left panel) and Rotarod Test (right panel) to evaluate the therapeutic efficacy of human HGF gene and hNgn1 gene-introduced MSCs in stroke animal model. As shown in FIG. 6, when PBS, HGF gene-introduced normal MSCs, and hNgn1 gene-introduced MSCs were transplanted at 4 weeks after stroke induction, no therapeutic efficacy was observed. On the contrary, when HGF gene and hNgn1 gene-introduced MSCs were transplanted, therapeutic efficacy was clearly observed.

The above results suggest that transplantation of HGF gene and hNgn1 gene-introduced MSCs in the stroke animal model shows excellent therapeutic efficacies on motor and sensory loss caused by brain injury in stroke model.

Figure 7:
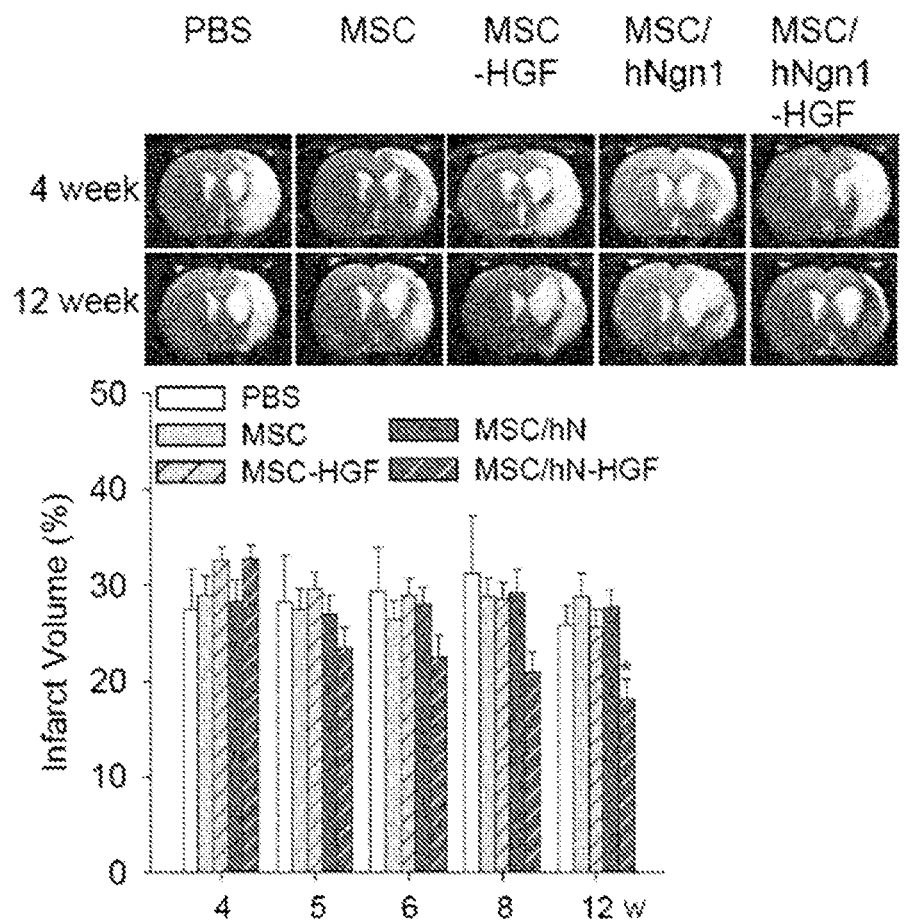
FIG. 7 is photographs showing the results of a MRI (upper panel) and quantitative analysis of the infarct region (lower panel) to evaluate the therapeutic efficacy of human HGF gene and human neurogenin 1 gene-introduced MSCs in stroke animal model.

In addition, the therapeutic efficacies of HGF gene and hNgn1 gene-introduced MSCs in the stroke animal model were examined by MRI (FIG. 7). FIG. 7 is photographs showing the results of the MRI (upper panel) and quantitative analysis of stroke lesion (lower panel) to evaluate the therapeutic efficacy of human HGF gene and hNgn1 gene-introduced MSCs in stroke animal model. As shown in FIG. 7, when PBS and neurogenin 1 gene-introduced MSCs were transplanted at 28 days after stroke induction, the infarct size was not reduced. On the contrary, when HGF gene and hNgn1 gene-introduced MSCs were transplanted, a reduction in the infarct size was observed.

The above results suggest that hNgn1 gene-expressing MSCs introduced with HGF gene shows excellent therapeutic efficacies on the brain infarction, compared to the hNgn1-expressing MSCs that were introduced with no HGF gene.

Example 7: Mechanism of Therapeutic Efficacy of HGF Gene and Human Neurogenin 1 Gene-Introduced MSCs in Stroke Animal Model In order to examine the mechanism of therapeutic efficacy of HGF gene and hNgn1 gene-introduced MSCs on the infarct region, tissue slices were prepared and analyzed by immunohistochemistry.

Example 7-1: Preparation of Tissue Slice

Eight weeks after transplantation, the albino rats were anesthetized as in Example 3-4 to extract the brains. The brains were post-fixed in the fixation solution at 4° C. for 16 hours. The post-fixed brains were sectioned with a thickness of 2 mm, dehydrated in an automated tissue processor, and infiltrated with xylene and paraffin. The tissues infiltrated with paraffin were embedded with paraffin, sectioned using a rotary microtome (Leica) with a thickness of 5 μm, and mounted to silane-coated slides. As a first stage of immunohistochemistry to recover tissue antigenicity, tissues were dipped in 10 mM sodium citrate, heated using a microwave at 99° C. for 10 minutes, and cooled at room temperature for 20 minutes.

Example 7-2: Immunohistochemical Staining

The tissue slices prepared in Example 7-1 were dipped in 1×PBS/0.1% Triton X-100 for 30 minutes. As a first stage of immunohistochemistry, they were reacted with normal goat serum at room temperature for 1 hour to block non-specific interaction. As primary antibodies, MAP2 and GFP antibodies diluted at 1:200 were used, and they were reacted at 4° C. for 16 hours. After washing three times with 1×PBS/0.1% Triton X-100 for 15 minutes, the sections were allowed to react with Alexa 488-conjugated anti-mouse IgG secondary antibody (Invitrogen, 1:250) to detect the MAP2 primary antibody and to react with Alexa 568-conjugated anti-mouse IgG secondary antibody (Invitrogen, 1:250) to detect the GFP primary antibody.

Figure 8:
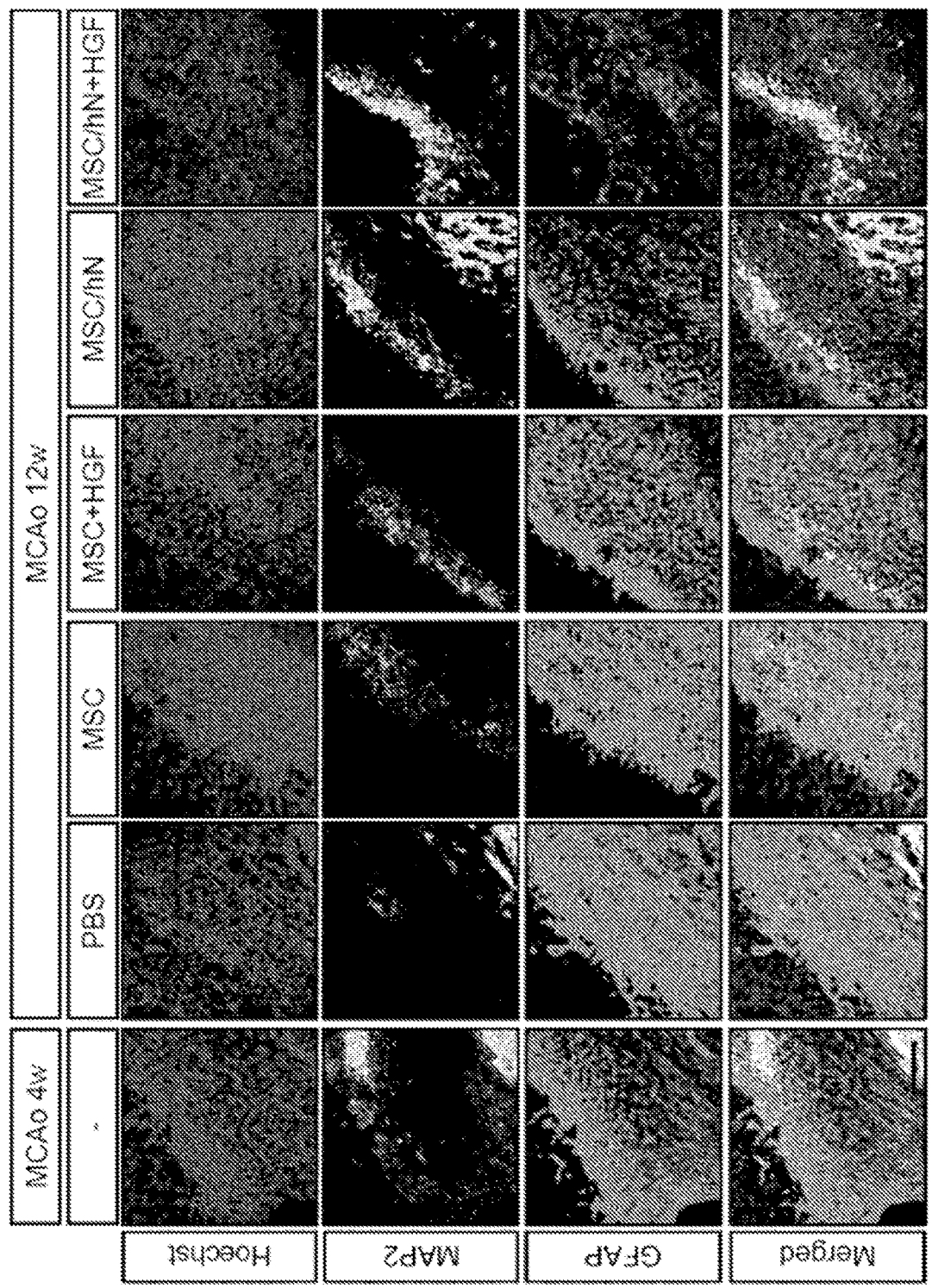
FIG. 8 is a photograph showing the result of immunohistochemistry using GFAP and MAP2 antibodies to examine glial cells and their expression pattern in the infarct region after transplantation of human HGF gene and human neurogenin 1 gene-introduced MSCs.

First, expression patterns of GFAP, a marker for glial cells mediating brain fibrosis, were examined (FIG. 8). FIG. 8 is a photograph showing the result of immunohistochemistry using GFAP and MAP2 antibodies to examine glial cells and their expression pattern in the infarct region after transplantation of human HGF gene and hNgn1 gene-introduced MSCs. As shown in FIG. 8, when PBS, HGF gene-introduced normal MSCs, and hNgn1 gene-introduced MSCs were transplanted in the infarct region at 4 weeks after stroke induction (MCAo), there were no changes in glial population at 12 weeks after stroke induction (MCAo). On the contrary, when HGF gene and hNgn1 gene-introduced MSCs were transplanted, distribution of glial cells was observed.

Next, the expression pattern of the neuronal marker, MAP2 was examined. As a result, transplantation of hNgn1 gene-introduced MSCs and transplantation of HGF gene and hNgn1 gene-introduced MSCs showed higher expression of neuronal cells, compared to the transplantation of PBS and HGF gene-introduced normal MSCs.

The above results suggest that hNgn1 gene-introduced MSCs were differentiated into neuronal cells, and HGF gene and hNgn1 gene-introduced MSCs inhibited population of glial cells involved in brain fibrosis, indicating that HGF gene and hNgn1 gene-introduced MSCs show therapeutic effects on chronic brain injury.

Figure 9:
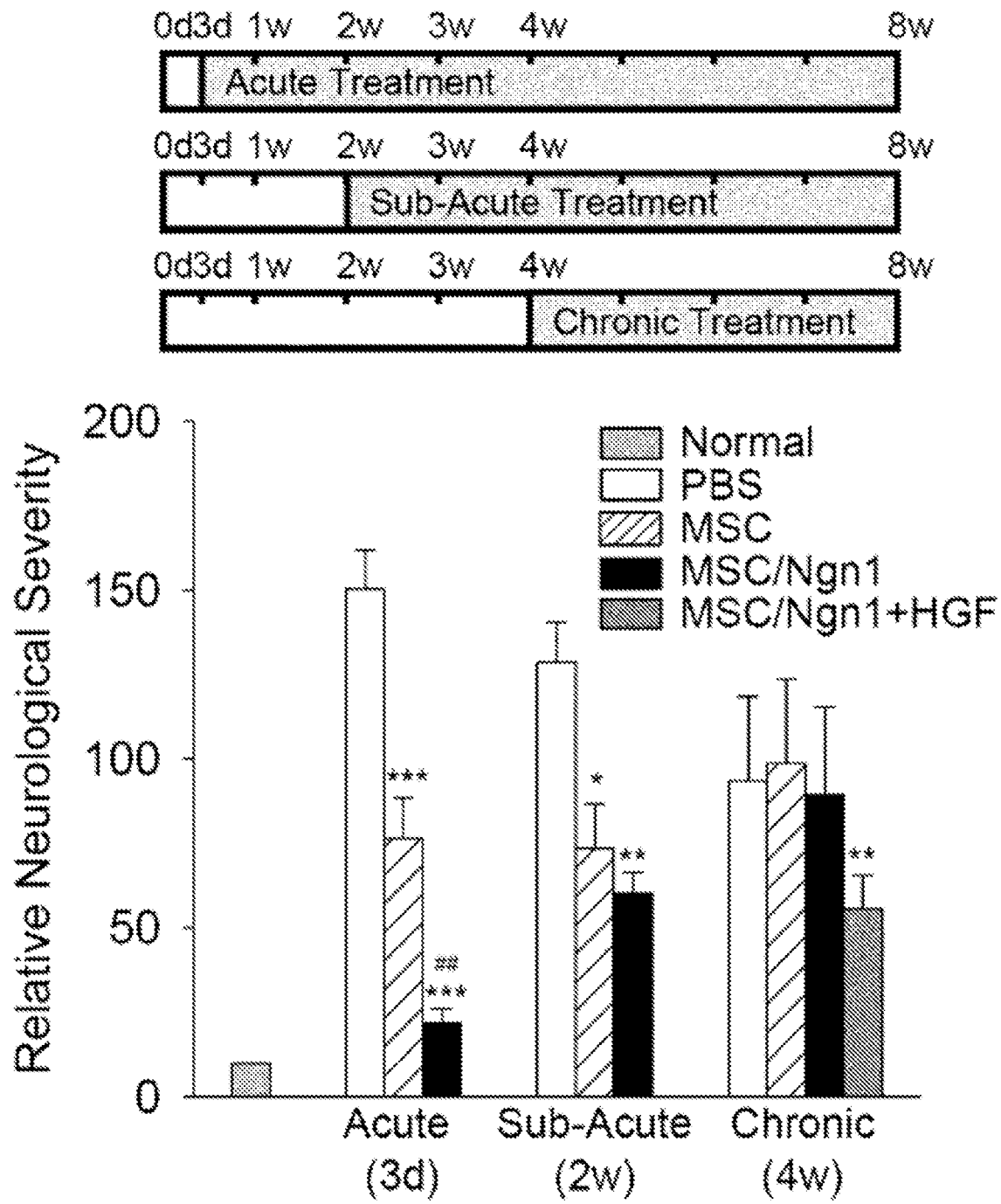
FIG. 9 is a diagram (upper panel) and a graph (lower panel) summarizing the therapeutic efficacies of the human HGF gene and human neurogenin 1 gene-introduced MSCs in stroke animal model according to the cell transplantation time.

Example 8: Therapeutic Effects of HGF Gene and Neurogenin 1 Gene-Introduced MSCs on Chronic Brain Injury Taken together, the HGF gene and neurogenin 1 gene-introduced MSCs showed therapeutic effects on chronic brain injury (FIG. 9). FIG. 9 is a diagram (upper panel) and a graph (lower panel) summarizing the therapeutic efficacies of the human HGF gene and hNgn1 gene-introduced MSCs in stroke animal model according to the cell transplantation time. As shown in FIG. 9, when therapeutic efficacies of neurogenin 1 gene-introduced MSCs in stroke animal model were examined according to the cell transplantation time, improved motor functions were observed when transplanted at 3 days (acute) and 2 weeks (subacute) after brain injury, compared to the PBS group, and no efficacies were observed when transplanted at 4 weeks after brain injury. However, neurogenin 1 gene and HGF gene-introduced MSCs showed high therapeutic efficacies even when transplanted at 4 weeks (chronic) after stroke.

Therefore, the above results suggest that HGF gene and hNgn1 gene-introduced MSCs show therapeutic effects on chronic brain injury.

The invention claimed is:

1. A method of transplanting autologous or allogeneic mesenchymal stem cells (MSCs) into the brain of a subject with chronic brain injury after stroke, said method comprising:
    (a) obtaining adult (MSCs);
    (b) culturing the adult MSCs;
    (c) transducing the cultured MSCs of step (b) with a viral vector comprising a nucleic acid sequence encoding the human hepatocyte growth factor (hHGF) as set forth in SEQ ID NO. 1 and a nucleic acid sequence encoding the human neurogenin 1 (hNgn1) as set forth in SEQ ID NO. 2;
    (d) selecting the transduced MSCs from step (c) that express hHGF and hNgn1; and
    (e) transplanting the selected MSCs from step (d) directly into the brain parenchyma of a subject, such that the MSCs are transplanted at or adjacent to a site of the chronic brain injury comprising an infarct region,
    wherein the step of transplanting is performed at least 4 weeks after the patient suffering a stroke, the patient thereby having chronic brain injury after stroke,
    wherein the transplanted MSCs are autologous or allogeneic to said subject, and
    wherein the transplanted MCSs express hHGF and hNgn1 and differentiate into neuronal stem cells expressing microtubule-associated protein-2 (MAP2), thereby resulting in inhibiting a population of glial cells involved in chronic brain fibrosis and a reduction in the size of the infarct region of the site of the chronic brain injury.

2. The method of claim 1, wherein the adult MSCs are derived from bone marrow.

3. The method of claim 1, wherein the viral vector is introduced into the adult MSCs via a retrovirus or an adenovirus vector.

4. A method of transplanting autologous or allogeneic mesenchymal stem cell (MSCs) into the brain of a subject with chronic brain injury after stroke, said method comprising:
    (a) obtaining adult MSCs;
    (b) culturing the adult MSCs;
    (c) transducing the adult MSCs of step (b) with a viral vector comprising a nucleic acid sequence encoding the human hepatocyte growth factor (hHGF) as set forth in SEQ ID NO. 1 and a nucleic acid sequence encoding the human neurogenin 1 (hNgn1) as set forth in SEQ ID NO. 2;
    (d) selecting the adult MSCs from step (c) that express hHGF and hNgn1; and
    (e) transplanting the selected adult MSCs from step (d) directly into the brain parenchyma of a subject having chronic brain injury after stroke, such that the MSCs are transplanted at or adjacent to a site of the chronic brain injury comprising an infarct region,
    wherein the transplanted MSCs are autologous or allogeneic to said subject, and
    wherein the transplanted MCSs differentiate into neuronal stem cells expressing microtubule-associated protein-2 (MAP2), thereby resulting in inhibiting a population of glial cells involved in chronic brain fibrosis and a reduction in the infarct size at the site of the chronic brain injury.

5. A method of transplanting autologous or allogeneic mesenchymal stem cell (MSCs) into the brain of a subject with chronic brain injury after stroke, said method comprising:
    transplanting adult human, bone marrow-derived, mesenchymal stem cell (MSCs) directly into the brain parenchyma of a human subject at least 4 weeks after the subject suffering a stroke, the subject having a chronic brain injury caused by the stroke,
    wherein a site of the chronic brain injury comprises an infarct region, the MSCs being transplanted at or adjacent the infarct region, wherein the transplanted MSCs are autologous or allogeneic to the subject, the MSCs being:
    transduced with:
    (i) a vector comprising a nucleic acid sequence encoding the human hepatocyte growth factor (hHGF) as set forth in SEQ ID NO. 1 and a nucleic acid sequence encoding the human neurogenin 1 (hNgn1) as set forth in SEQ ID NO. 2;
    or
    (ii) a first vector comprising a nucleic acid sequence encoding the hHGF as set forth in SEQ ID NO. 1 and a second vector comprising a nucleic acid sequence encoding the hNgn1 as set forth in SEQ ID NO. 2, and
    the transduced MSCs selected to express hHGF and hNgn1, and the transplanted MSCs expressing hHGF and hNgn1 differentiate into neuronal cells expressing microtubule-associated protein-2 (MAP2), resulting in a reduction in the size of the infarct region.

* * * * *

SEQUENCE LISTING

```
<160> NUMBER OF SEQ ID NOS: 2

<210> SEQ ID NO 1
<211> LENGTH: 2187
<212> TYPE: DNA
<213> ORGANISM: Homo sapiens

<400> SEQUENCE: 1
atgtgggtga ccaaactcct gccagccctg ctgctgcagc atgtcctcct gcatctcctc      60
ctgctcccca tcgccatccc ctatgcagag ggacaaagga aagaagaaa  tacaattcat     120 gaattcaaaa aatcagcaaa gactacccta atcaaaatag atccagcact gaagataaaa     180
accaaaaaag tgaatactgc agaccaatgt gctaatagat gtactaggaa taaaggactt     240
```

-continued

```
ccattcacttgcaaggctttt gttttttgat aaagcaagaa acaatgcct  ctggttcccc    300
ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta gagtggcat  caaatgtcag ccctggagtt ccatgatacc acacgaacac    480
agcttttgc  cttcgagcta tcggggtaaa gacctacagg aaaactactg tcgaaatcct    540
cgagggaag  aaggggacc  ctggtgtttc acaagcaatc cagaggtacg ctacgaagtc    600
tgtgacattc ctcagtgttc agaagttgaa tgcatgacct gcaatgggga gagttatcga    660
ggtctcatgg atcatacaga atcaggcaag atttgtcagc gctgggatca tcagacacca    720
caccggcaca aattcttgcc tgaaagatat cccgacaagg gctttgatga taattattgc    780
cgcaatcccg atggccagcc gaggccatgt tgctatactc ttgaccctca cacccgctgg    840
gagtactgtg caattaaaac atgcgctgac aatactatga atgacactga tgttcctttg    900
gaaacaactg aatgcatcca aggtcaagga gaaggctaca ggggcactgt caataccatt    960
tggaatggaa ttccatgtca gcgttgggat tctcagtatc ctcacgagca tgacatgact   1020
cctgaaaatt tcaagtgcaa ggacctacga gaaaattact gccgaaatcc agatgggtct   1080
gaatcaccct ggtgttttac cactgatcca acatccgag  ttggctactg ctcccaaatt   1140
ccaaactgtg atatgtcaca tggacaagat tgttatcgtg ggaatggcaa aaattatatg   1200
ggcaacttat cccaaacaag atctggacta acatgttcaa tgtgggacaa gaacatggaa   1260
gacttacatc gtcatatctt ctgggaacca gatgcaagta agctgaatga gaattactgc   1320
cgaaatccag atgatgatgc tcatggaccc tggtgctaca cggaaatcc  actcattcct   1380
tgggattatt gccctatttc tcgttgtgaa ggtgatacca cacctacaat agtcaattta   1440
gaccatcccg taatatcttg tgccaaaacg aaacaattgc gagttgtaaa tgggattcca   1500
acacgaacaa acataggatg gatggttagt ttgagataca gaaataaaca tatctgcgga   1560
ggatcattga taaaggagag ttgggttctt actgcacgac agtgtttccc ttctcgagac   1620
ttgaaagatt atgaagcttg gcttggaatt catgatgtcc acggaagagg agatgagaaa   1680
tgcaaacagg ttctcaatgt tcccagctg  gtatatggcc ctgaaggatc agatctggtt   1740
ttaatgaagc ttgccaggcc tgctgtcctg gatgattttg ttagtacgat tgatttacct   1800
aattatggat gcacaattcc tgaaaagacc agttgcagtg tttatggctg ggctacact   1860
ggattgatca actatgatgg cctattacga gtggcacatc tctatataat gggaaatgag   1920
aaatgcagcc agcatcatcg agggaaggtg actctgaatg agtctgaaat atgtgctggg   1980
gctgaaaaga ttggatcagg accatgtgag ggggattatg gtggcccact tgtttgtgag   2040
caacataaaa tgagaatggt tcttggtgtc attgttcctg gtcgtggatg tgccattcca   2100
aatcgtcctg gtattttgt  ccgagtagca tattatgcaa aatggataca caaaattatt   2160
ttaacatata aggtaccaca gtcatag                                       2187
```

<210> SEQ ID NO 2
<211> LENGTH: 716
<212> TYPE: DNA
<213> ORGANISM: Homo sapiens

<400> SEQUENCE: 2

```
atgccagccc gccttgagac ctgcatctcc gacctcgact gcgccagcag cagcggcagt     60
gacctatccg gcttcctcac cgacgaggaa gactgtgcca gactccaaca ggcagcctcc    120
gcttcggggc cgcccgcgcc ggcccgcagg agcgcgccca atatctcccg ggcgtctgag    180
```

-continued

```
gttccagggg cacaggacga cgagcaggag aggcggcggc gccgcggccg gacgcgggtc    240
cgctccgagg cgctgctgca ctcgctgcgc aggagccggc gcgtcaaggc caacgatcgc    300
gagcgcaacc gcatgcacaa cttgaacgcg gccctggacg cactgcgcag cgtgctgccc    360
tcgttccccg acgacaccaa gctcaccaaa atcgagacgc tgcgcttcgc ctacaactac    420
atctgggctc tggccgagac actgcgcctg gcggatcaag ggctgcccgg aggcggtgcc    480
cgggagcgcc tcctgccgcc gcagtgcgtc ccctgcctgc ccggtccccc aagcccgcc    540 agcgacgcgg agtcctgggg ctcaggtgcc gccgccgcct ccccgctctc tgacccagt    600 agcccagccg cctccgaaga cttcacctac cgccccggcg accctgtttt ctccttccca    660
agcctgccca aagacttgct ccacacaacg ccctgtttca ttccttacca ctaggc       716
```